(12) United States Patent
Schreier et al.

(10) Patent No.: US 6,451,559 B1
(45) Date of Patent: Sep. 17, 2002

(54) EXPRESSION VECTOR FOR IMPROVED PRODUCTION OF POLYPEPTIDES IN YEAST

(75) Inventors: Thomas Schreier; Rainer Voegeli, both of Bubendorf (CH)

(73) Assignee: Pentapharm AG, Basel (CH)

( * ) Notice: Subject to any disclaimer, the term of this patent is extended or adjusted under 35 U.S.C. 154(b) by 0 days.

(21) Appl. No.: 09/518,658

(22) Filed: Mar. 3, 2000

Related U.S. Application Data

(63) Continuation of application No. PCT/EP97/04289, filed on Sep. 5, 1997.

(51) Int. Cl.⁷ .......................... C12P 21/02; C12N 1/16; C12N 15/63; C12N 15/64; C12N 15/81
(52) U.S. Cl. .................. 435/69.1; 435/71.1; 435/91.42; 435/254.2; 435/320.1; 435/483
(58) Field of Search .............................. 435/320.1, 91.4, 435/91.41, 91.42, 91.2, 91.5, 483, 71.1, 69.1

(56) References Cited

U.S. PATENT DOCUMENTS

| | | | |
|---|---|---|---|
| 5,432,082 A | | 7/1995 | Galeotti et al. |
| 5,541,098 A | * | 7/1996 | Caput et al. ................. 435/191 |
| 5,637,504 A | * | 6/1997 | Hinchliffe et al. .......... 435/69.1 |
| 5,646,037 A | * | 7/1997 | Buxton et al. ......... 435/252.33 |

FOREIGN PATENT DOCUMENTS

| | | |
|---|---|---|
| CA | 2031810 | 6/1999 |
| EP | 0 252 561 A | 1/1988 |
| EP | 0 284 044 A | 9/1988 |
| EP | 0431543 | 6/1991 |
| WO | WO88/08027 | * 10/1988 |

OTHER PUBLICATIONS

Bermingham–McDonogh et al. 1988. PNAS USA 85:4789–4793.*

Cesareni et al. 1987. in Genetic engineering: principles and methods. vol. 9. J.K. Setlow, ed. Plenum Press. pp. 135–154.*

Sambrook et al. 1989. Molecular Cloning, a laboratory manual. Cold Spring Harbor Laboratory Press. pp. 1.25–1.28, 1.68–1.71, 1.85, 5.2, 5.31, 5.34–5.35.*

Rose et al. 1990. pp. 234–279. in Methods in Enzymology, vol. 185, Gene Expression Technology. Goeddel (ed.) Academic Press, Inc. 1991.*

* cited by examiner

Primary Examiner—Terry McKelvey
(74) Attorney, Agent, or Firm—Pennie & Edmonds, LLP

(57) ABSTRACT

A new expression vector for the production of a polypeptide in yeast. The vector includes a sequence coding for the polypeptide and other sequences allowing expression of the polypeptide only in yeast. The other sequences lack any non-yeast sequences. Other embodiments include a yeast strain comprising such a vector, a method for the production of the vector, a method for the production of the yeast strain by transformation of a yeast strain with the new vector, and a method for the production of a polypeptide in the transformed yeast strain by fermentation thereof followed by isolation of the polypeptide.

21 Claims, 3 Drawing Sheets

US 6,451,559 B1

EXPRESSION VECTOR FOR IMPROVED PRODUCTION OF POLYPEPTIDES IN YEAST

CROSS-REFERENCE TO RELATED APPLICATIONS

This application is a continuation of the U.S. phase of co-pending International Application No. PCT/EP97/04289, filed Sep. 5, 1997.

FIELD OF THE INVENTION

The invention relates to a new expression vector for the production of a polypeptide in yeast, a yeast strain being transformed with such vector, and methods for the production of the vector, yeast strain and polypeptide.

BACKGROUND OF THE INVENTION

Genetic engineering techniques for expression in yeasts commonly use shuttle vectors. The shuttle vectors have nucleotide sequences coding for a particular polypeptide combined with sequences necessary for expression in yeast, such as a yeast promoter. These shuttle vectors also have additional sequences that allow for expression in bacteria, such as *Escherichia coli*, or other microorganisms. Such additional non-yeast sequences are useful only for the construction of the vectors. However, they are superfluous for the expression in yeast. In fact they may hinder the efficient expression of the polypeptide in yeast or retard the replication of the organism because the superfluous nucleotides must also be doubled, which is an energy consuming process.

The yeast *Saccharomyces cerevisiae* is usually an excellent microorganism for the production of both homologous and heterologous proteins. This is because of its well characterized genetic system, rapid growth, and technical advantages of manipulation. Additionally, the development of DNA transformation systems for the introduction of cloned genes and their inexpensive and safe overproduction in simple fermentation conditions, has made this organism particularly useful for large-scale industrial practice.

A number of yeast polypeptides are known in the art. Of particular interest are the superoxide dismutases. The yeast *Saccharomyces cerevisiae* contains two species of superoxide dismutases (EC 1.15.11), the copper/zinc-(Cu/Zn SOD) and the manganese-(Mn SOD) containing forms. The Cu/Zn SOD is localized in the cytoplasm while the manganese enzyme is restricted to the mitochondrial matrix. This enzyme is assumed to provide in vivo protection against toxic free radicals generated within cells as intermediates of normal metabolism (Bilinski, T. et al. *Biochem. Biophys. Res. Commun.* 130: 533–539 (1985), Van Loon A.P.G.M. et al. *Proc. Natl. Acad. Sci. USA* 83: 3820–3824 (1986), Lee F. J. et al. *J Free Rad. Biol. Med.* 1:3 19–325 (1985), Galiazzo F. et al. *Biochim. Biophys. Acta* 965: 46–51 (1988)). Consequently, it is expected to be useful for preventing or treating potential damage in human, particularly damage from cell aging and senescence (Rosen D. R. et al. *Nature* 362, 59–62 (1993), McCord J. M. and Fridovich I. *J Biochem* 244: 6049–6055 (1969),. McCord J. M. et al. *Proc. Natl. Acad. Sci. USA* 68: 1024–1027 (1971), McCord J. M. *N. Engl. J Med.* 312: 159–163 (1985)).

The Cu/Zn SOD gene from Saccharomyces cerevisiae was cloned, sequenced (Bermingham-McDonogh O., et al. *Proc. Nat. Acad. Sci. USA* 85: 4789–4793 (1988)), and the structure and mechanism of action of the enzyme is well characterized (Djinovic K. et al. *J. Mol. Biol.* 225: 791–809 (1992), O'Neill P. et al. *Biochem. J* 251: 41–46 (1988)). The Cu/Zn SOD is an abundant metalloenzyme present in the cytoplasm of most aerobic and many anaerobic organisms, whose activity catalyzes the dismutation of the superoxide anion to dioxygen and hydrogen peroxide.

It is an object of the present invention to improve on the yields of polypeptides in the fermentation processes of yeasts transformed with expression vectors coding for such polypeptides. It is a further object to provide new vectors which are able to express desired polypeptides in yeast in larger amounts as compared to previous processes. A further object is to provide new yeast strains transformed with such vectors that are superior compared to the wild-type strain or those which are transformed with shuttle vectors.

SUMMARY OF THE INVENTION

The present invention provides for expression vectors and a yeast strains. In particular a *Saccharomyces cerevisiae* strain transformed with a vector, which produces higher levels of yeast or non-yeast polypeptides compared to the wild-type strain or those transformed with a shuttle vector. Methods for the preparation of such expression vector, yeast strains and endogenous yeast polypeptides are set forth.

Numerous aspects and advantages of the invention will be apparent to those skilled in the art upon consideration of the detailed description and the drawings of the invention which provides illustrations of the practice of the invention in its embodiments.

DETAILED DESCRIPTION OF THE INVENTION

Figure 1:
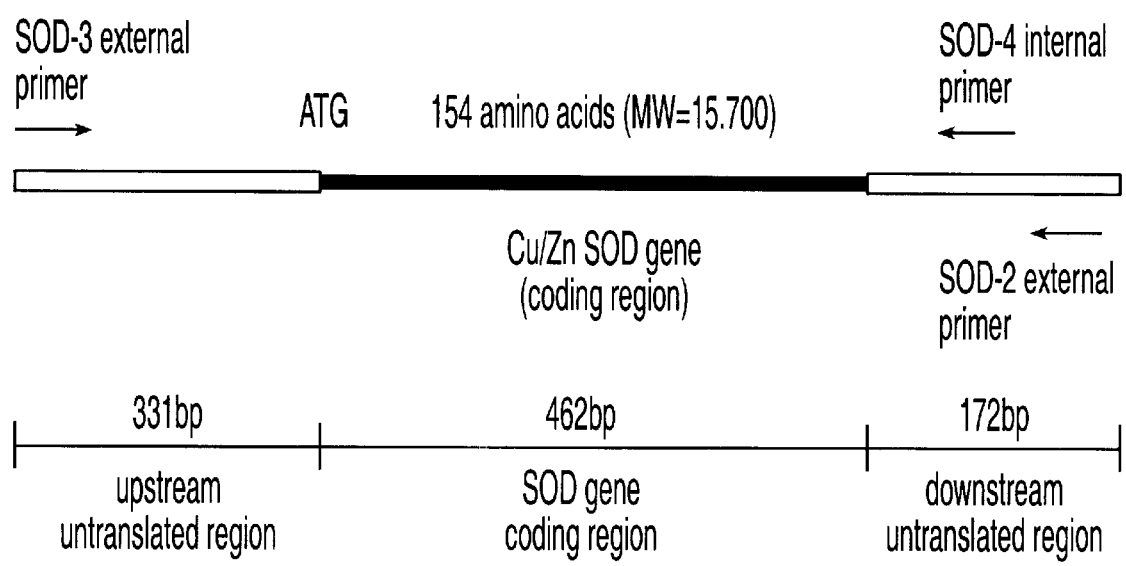
FIG. 1. Depiction of the coding region for the Cu/Zn SOD gene from yeast strain S288C with the positions of the external primers SOD3 and SOD2 and the internal primer SOD4 designated in the upstream and downstream regions of the SOD gene locus.

In the present invention the following primer DNA sequences have been used, the structures of which are precisely shown in the Sequence Identification Listing (the bp regions of the primers were taken from the EMBL vector, GeneBank accession No. J03279):

SEQ ID NO 1: is the external primer SOD-3, upstream region 81–102 bp

SEQ ID NO 2: is the external primer SOD-2, downstream region 10 18–1036 bp

SEQ ID NO 3: is the internal primer SOD-4, region 97 1–991 bp

A preferred embodiment of the present invention is a new expression vector for producing polypeptides in yeast comprising the coding sequence for said polypeptide, and additional sequences that allow for expressing the polypeptide in yeast, these additional sequences lack any non-yeast sequences.

The term "expression vector" is intended mean a vector, in particular a DNA vector, such as a plasmid, which comprises a sequence coding for a polypeptide, a promoter sequence in reading frame with the coding sequence, and optionally other sequences, which are needed for efficiently producing or using the vector, such as an origin of replication (ori), a leader sequence, a terminator and a selection marker. Such optional other sequences are only derived from yeasts and are well known in the art.

The sequence coding for said polypeptide may be a yeast or non-yeast sequence. Yeast sequences may code for yeast polypeptides with enzyme functions. Examples of Yeast enzymes include antioxidative enzymes like superoxide dismutase (SOD), thiol specific antioxidant (TSA), and cytochrome c peroxidase, proteases like cerevisin precursor PRB 1, proteinase inhibitors including proteinase B inhibitor 2, cytokines, and various others.

Sequences coding for non-yeast polypeptides may be derived from any living organism, particularly humans and animals. Such polypeptides are preferably useful in the medical arts and include but are not limited to human insulin, tissue plasminogen activator, interferons, erythropoietin, growth factors like keratinocyte growth factor, tryptase, Protein C activator, tissue inhibitors of metalloproteinases (TIMP's), elastase inhibitors, and various others. The sequences coding for such useful polypeptides are known in the art.

All these sequences are under the control of yeast promoters. Useful yeast promoters include the GAL/CYC promoter for example and are known in the art.

The final vector of the invention is only replicable in yeast cells. With the exception of the non-yeast sequence coding for any desired non-yeast polypeptide, the vector lacks any non-yeast sequences.

A preferred vector according to the invention is a yeast plasmid comprising the Cu/Zn SOD gene which is under the control of the GAL/CYC promoter, and is in particular the plasmid named pEMBL-SOD, without multiple cloning site or *Escherichia coli* sequences.

This plasmid may be used as a starting plasmid for constructing an expression vector where the Cu/Zn SOD gene is exchanged for sequences coding for other polypeptides.

In a further embodiment the invention provides a method for the production of the new expression vector defined hereinbefore. The method for producing the new expression vector of the invention is characterized by the excision of any non-yeast sequences from a shuttle vector able to express a polypeptide in a yeast strain. Optionally, the sequence coding for said polypeptide is replaced by a sequence coding for another polypeptide.

The new expression vectors are obtained by conventional techniques from known shuttle vectors, such as yeast integration plasmid YIp, yeast replication plasmid YRp, yeast centromeric plasmid YCp, the yeast episomal plasmid YEp. The new expression vectors comprise a polypeptide gene and lack any non-yeast DNA sequences.

The starting shuttle vectors may already have the sequence coding for the desired polypeptide under the control of any yeast promoter, like the GAL/CYC promoter. Such vectors are for example the plasmid pEMBL-SOD 374 or pEMBL-SOD ATG. These plasmids are used as intermediates for the production of the final vector according to the invention. If the gene is not yet available, constructing the vector starts with the isolating the gene coding for the desired polypeptide from a known source, e. g., from a human or animal or a wild-type microorganism strain. The gene is multiplied through PCR with synthetic primers, and inserted into the vector, usually a shuttle vector. Using restriction enzymes, all non-yeast sequences including but not limited to bacterial sequences, multiple cloning sites, bacterial origins of replication (ORIs), selectable markers, the origin of replication of the filamentous bacteriophage fl, the ampicillin resistant gene, and the like are deleted from the intermediate vectors.

The following is a more detailed discussion of the method used: Gene expression requires placing a gene, coding for a polypeptide of interest, under the control of a strong yeast promoter that directs synthesis of the corresponding messenger RNA. The DNA regulatory elements required for expression are carried by yeast vectors.

These vectors are shuttle vectors that may be propagated in yeast strains as well as in the bacterium *Escherichia coli* for convenient manipulations and large scale preparations of the different intermediate plasmids.

A number of different yeast integrating (Yip), replicating (YRp), centromere (YCp) and episomal (YEp) plasmid vectors have been developed (Rose A. B., Broach J. R. *Methods in Enzymology*, 185: 234–279 (1990), Schneider J. C., and Guarente L. *Methods in Enzymology*, 194: 373–388 (1991)).

The plasmid that was chosen for the expression of the Cu/Zn SOD gene is the specific YEp (yeast episomal plasmid) shuttle vector pEMBLyex4 of 8.800 base pairs (Cesarani and Murray, in Setlow J. K. (ed) *Genetic Engineering: Principle and Methods*, Volume 9, Plenum Press, N.Y. 134–135 (1987)).

Such a vector carries the 2-micron yeast episome (a small double-stranded DNA plasmid present in the nuclei of most *Saccharomyces cerevisiae* strains) which provides high mitotic stability and the ability to be autonomously replicated (Murray, J. A. H., *Mol. Microbiol.*, 1: 1–4 (1987), Hartley and Donelson, Nature, 286: 860–864 (1980), Clark-Walker G. D., and Miklos G. L. G., *Eur. J Biochem.*, 41: 359–365 (1974), Futcher A. B., and Cox B. S., *J. Bacteriol.*, 157: 283–290 (1984)).

The persistence of the plasmid is due to the presence, in the 2-micron moiety, of the REP 3 locus (for the partitioning of the plasmid during cell division) and the ARS sequence (origin of replication).

The plasmid pEMBLyex4 carries the LEU 2 and URA 3 selectable markers which are extremely useful both to select the initial yeast cell transformants and to provide constant pressure to maintain the plasmid in the yeast cell (Alani E. et al., *Genetics*, 116: 541 (1987), Gritz L., and Davies J., *Gene*, 25: 179 (1983), Kaster K. R., et al., *Curr. Genet.*, 8: 353 (1984), Rine J., et al., *Proc. Natl. Acad. Sci. USA*, 80:6750 (1983)).

In general, however, these kinds of plasmids achieve a good maintenance even in the absence of positive selection. In such a situation, cells can lose the plasmid at a rate of about 4 percent per generation. The pEMBLyex4 forms part of a special class of 2-micron vectors with a very high copy number (about 100–200 per cell).

Moreover, yeast strains lacking the 2-micron episome (ciro) to propagate the plasmid were used. The stability of pEMBLyex4 in such strains is known to be very high even without continued selection pressure.

The pEMBLyex4 plasmid includes the entire yeast expression hybrid cassette UAS GAL/CYC. The promoter cassette contains an upstream activation site (UAS sequence) and the promoter region (TATA box) for both high levels of transcription of the downstream gene and regulation of expression. The pEMBLyex4 plasmid also includes a multiple cloning site (MCS) for inserting the gene and a termination region (Guarente L. et al., *Proc. Natl. Acad. Sci., USA*, 79: 7410–7414 (1982)). The hybrid cassette UAS GAL/CYC has from 5' to 3' the following regions:

- a 365 bp fragment (Sau3A-XhoI) from the upstream activation sequence of the region between the yeast GAL4 and GAL 10 genes which contains the binding region for the GAL4 product;
- a 250 bp region (XhoI-SstI) containing the promoter of the yeast gene CYC1, which carries the TATA box and the mRNA start sites but without the ATG region;
- a polylinker (SstI-HindlII) of 95 bp with unique restriction enzyme sites;
- a 250 bp region (in a HindIII-SnaBI fragment) carrying polyadenylation and transcription terminator signals, from the 2-micron FLP gene.

The expression system is regulated by the GAL4 and GAL8O gene products. The GAL4 protein is a transcriptional activator that binds to the UAS gal sequences. The activity of the GAL4 protein is inhibited by the binding of the GAL8O protein to its carboxy-terminal region. The system is repressed by glucose, which inhibits the binding of GAL4 protein to the UASgal, and is induced by galactose, which causes the dissociation of the GAL8O protein from the GAL4 protein.

In a further embodiment the invention provides a novel yeast strain transformed with an expression vector according to the invention.

Yeast species are any known species useful for the expression of yeast or non-yeast polypeptides, for example *Saccharomyces cerevisiae* or *Saccharomyces occidentalis*, or non Saccharomyces yeast species, e. g., *Hansenula polymorpha, Pichia pastoris, Schwanniomyces occidentalis*, and *Pichia stipitis*.

A preferred novel yeast strain is, for example *Saccharomyces cerevisiae*, with improved ability to synthesize the Cu/Zn SOD enzyme through insertion of the relative homologous gene in the intracellular compartment.

Preferred intermediate yeast strains according to the present invention are for example GRF 18 transformed with plasmid pEMBL-SOD 374 or plasmid pEMBL-SOD ATG which have been produced, isolated and characterized.

A further object of the invention is a method for the production of a yeast strain transformed with an expression vector coding for an endogenous yeast polypeptide, lacking any non-yeast sequences. This yeast strain is able to overproduce said yeast polypeptide and is characterized in that it it is transformed with a new vector described hereinbefore.

The transformation follows methods common in the art, such as the LiCl method of Ito et al., as modified by R. H. Schiestl et al. (1989), *Current Genetics*, 16, 339–346, or the method of Hinnen et al., (1978), *Proc. Natl. Acad. Sci. USA*, 75, 1929–1933.

In a further embodiment, the invention provides a method for the production of a polypeptide in a yeast strain comprising fermentation of a yeast strain transformed with an expression vector according to the invention.

Fermentation follows methods common in the art, such as the fed-batch method with a controlled fed of glucose during the growth phase and induction of expression by addition of galactose in the middle of the growth phase according to Alberghina, L., et al., (1991), *Biotech. and Appl. Biochem.*, 14, 82–92.

EXAMPLES

The following examples are presented by way of illustration of the invention and are directed to procedures carried out for the isolation and characterization of a yeast enzyme gene: the Cu/Zn SOD gene from traditional strains of *S. cerevisiae*. Examples are provided for procedures for expressing yeast enzymes encoded by their genes in yeast strains under the control of a strong yeast promoter, and to the development and characterization of a yeast strain able to produce high levels of the enzyme; the SOD protein is used as an example.

Abbreviations

Hereinbefore and hereinafter the following abbreviations are used:

| | |
|---|---|
| ARS | Autonomously Replicating Sequence |
| EDTA | ethylenediamine tetra acetic acid |
| EMBL | European Molecular Biology Laboratory |
| LB | Luria Bertani Medium |
| MCS | multiple cloning site |
| PCR | polymerase chain reaction |
| PIU | Pyrogallol Inhibitory Units |
| REP | Replikon (short DNA-sequence which serves in cells as origin of DNA replication) |
| SDS | sodium dodecyl sulfate |
| SOD | superoxide dismutase |
| TBE | Tris-Borate-EDTA buffer |
| TE | Tris-EDTA buffer |
| w/oColi | without *Escherichia coli* sequences |
| w/oMCS | without multiple cloning site |
| YCp | yeast centromeric plasmid |
| YEp | yeast episomal plasmid |
| YEPD | Yeast Extract-Peptone-Dextrose medium |
| YIp | yeast integration plasmid |
| Yrp | yeast replication plasmid |

Example 1

Extraction and Purification or Yeast Genomic DNA

This example relates to the extraction and purification of yeast genomic DNA to be used for the isolation of the yeast Cu/Zn SOD gene.

The DNA source to used to isolate the Cu/Zn SOD gene can be any wild-type yeast strain. In this specific case DNA was extracted from Saccharomyces cerevisiae strains S288C wild-type, ga12, and W309 wild-type.

Similar DNA extraction could be performed by using other wild-type yeast species a DNA source, for example W303.

The haploid yeast strain S288C is a typical strain that is currently used in most of the Molecular Biology laboratories around the world for the isolation of yeast genes, and genetic and biochemical studies (Mortimer R. K. and Johnson J. R., *Genetics*, 113:13 (1986)). The strain W309 has been considered as a potential alternative source. Both strains are known to carry a copy of the wild-type Cu/Zn SOD gene in their genome. The strains were provided by The Departement of Physiology and General Biochemistry, University of Milan.

A modified protocol for extracting total yeast genomic DNA according to methods of Cryer, Ecclesial and Marmur, *Methods Cell Biology*, 12:39–44 (1975) was used as follows.

Yeast cells, from a petri plate with YEPD medium, were inoculated in 200 mL of complete medium YEPD (1% Bacto-yeast extract, 2% Bacto-peptone, 2% Dextrose) and grown in a 1 liter flask, overnight with shaking at 300° C., until late exponential phase (about 8×10⁷cells/mL).

A total of 8×10⁸ cells were used for the extraction of the DNA. 10 mL of cells were spun down and concentrated in a polypropylene tube and the pellet was transferred to a 1.5 mL Eppendorf tube. 300 microliters of lysis buffer (NaCl 0.15 M, EDTA 0.1 M pH 8, SDS 1%) and 300 microliters of glass microbeads (diameter of 0.5 mm) were added to the Eppendorf tube. The cells were vortexed five times on ice, with pauses of 1 min.

The cell suspension was homogenized by vortexing with 600 microliters of phenolchloroform-TE solution and spun for 2 min. The upper aqueous phase was transferred to a new Eppendorf tube and 600 microliters of chloroform-isoamylic-alcohol solution (24:1) was added and mixed.

The upper phase was transfered to a new tube and incubated at 37° C. for 30 min with RNAase at a final concentration of 1 mg/mL. After ethanol precipitation, the pellet was resuspended in TE buffer (Tris 10 mM, EDTA 1 mM, pH 8).

About 100 mg of yeast genomic DNA, at about 1 mg/mL, was obtained from each preparation following this method. This was enough for many experiments.

Example 2

Isolating the Chromosomal Region Carrying the Cu/Zn SOD Gene

Polymerase Chain Reaction (PCR) was used to isolate the chromosomal region carrying the Cu/Zn SOD gene.

The Cu/Zn SOD gene maps to the right arm of chromosome X in *S. cerevisiae* between the cyc1-rad6-SUP4-cdc8 cluster and cdc11 region (Chang et al. *J Biol Chem.* 266: 44 17–4424 (1991). It has no introns in its coding sequence. Consequently, it is possible to isolate the entire translated region directly from genomic DNA by PCR. In addition, both the 5' upstream region and the 3' downstream region of the gene are known.

To perform the PCR reaction, pairs of synthetic oligonucleotide primers which span the SOD gene between the upstream and the downstream region are needed.

The primers for the PCR were designed using the OLIGO primer analysis software, Version 4.0 (National Biosciences Inc. Plymouth) to cover the region of the published Cu/Zn SOD gene sequence of 1037 bases in Berminghan-McDonogh O., Gralla E., Valentine J., *Proc. Natl. Acad. Sci. USA* 85:4789 (1988) (EMBL/Gene Bank, Accession No. J03279).

The primers were synthesized on an Applied Biosystem 392 Nucleic Acid synthesizer (Perkin-Elmer Corp., Foster City, Calif.) and purified by gel filtration with Sephadex G-25 DNA grade NAP-25 Columns (Pharmacia P-L Biochemicals Inc; Milwaukee, Wis.).

As a general strategy aimed to increase the chance for isolating the Cu/Zn-SOD gene from the yeast genome the so called "semi-nested PCR" was used. This strategy uses a twostep protocol requiring three different primers (FIG. 1).

The first step, which uses two primers (one upstream and one downstream primer, SOD-3 and SOD-2), allows for the amplification of a larger region of the genome. This step is followed by a second amplification, which uses a new internal primer (SOD-4) and one of the previous two (SOD-3), which finally permits the isolation and recovery of the SOD gene.

The first round of PCR amplification was performed using the following primers: SOD-3 (upstream primer, region 81–102 of the sequence entered in EMBL/Gene Bank, Accession No. J03279):

SEQ. ID NO:1 5'-GGA CGT AAG CAT CTC TGA AGT G -3' (22mer, $T_M$=66° C.),

SOD-2 (downstream primer, region 1018–1036 of the sequence entered in EMBL/Gene Bank, Accession No. J03279), SEQ. ID NO:2 5'- GCC GTC GAC GGA CCC CTC AAG ACC CCT C -3' (28 mer, $T_M$=64° C.).

The SOD-2 primer has a matching region of 19 bases of length ($T_M$ 64° C.) and a 5'-non-matching region which carries a BaniHI restriction site.

DNA amplification was performed in 50 mM KCl, 10 mM Tris-HCl pH 8.3, 1.5 mM $MgCl_2$, 500 mM of each deoxynucleotide (dATP, dCTP, dGTP, dTTP), 0.5 mM of each primer, 50 or 100 ng of genomic DNA and 2.5 Units of Taq DNA polymerase (Perkin-Elmer Corp.) in an 100 mL reaction volume. Times and temperatures used in each amplification stage were as follows: 1 min at 94° C. for the denaturation, 1.5 min at 63° C. for the annealing and 2 min for the elongation.

The PCR reaction generated a DNA fragment of 965 base pairs (bp) in length, as seen in agarose gel electrophoresis, which may include the entire coding sequence of the SOD gene of 462 bp, an upstream sequence of 331 bp and a downstream sequence of 172 bp.

The second round (semi-nested PCR) was performed using the primer SOD-3 and a third internal primer SOD-4 which spans the region 971–991 of the sequence entered in EMBL/Gene Bank, accession No. J03279 and has the following sequence:

SEQ ID NO:3 5'- GCC GTC GAC ACA CTT GGT GAA TGA TCA AGG -3'.

Primer SOD-4 has a matching region of 21 bases of length ($T_M$=60° C.) and a 5' non-matching region which carries a SalI restriction site.

The semi-nested PCR reaction, performed with the above conditions except for the annealing temperature of 60° C., generated a shorter DNA fragment of 920 base pairs (bp) of length which may include the entire coding sequence of the SOD gene of 462 bp, an upstream sequence of 331 bp, and a downstream sequence of 127 bp.

Example 3

Subcloning of the Cu/Zn SOD Gene Into the Plasmid Vector pCRII

This example relates to the subcloning of the Cu/Zn SOD gene into the plasmid vector pCRII.

Following amplification, the products of the reactions were loaded on a 1.2% low-melting temperature agarose gel and run on an electrophoresis apparatus (MiniSubgel DNA cell, BIO-RAD Laboratories, Inc. Hercules, Calif., USA,). The appropriate DNA band was then isolated from the agarose gel through standard methods and purified by phenol extraction (Sambrook J., Fritsch E. F., and Maniatis T. *Molecular Cloning. A manual laboratory*, Cold Spring Harbor Laboratory, N.Y. 1989).

Finally, the purified DNA fragment was inserted in the multiple cloning site (MCS) of the linearized plasmid pCRII of 3932 bp of length using the TA Cloning System (Invitrogen Corp. San Diego, Calif.), by ligation with T4 DNA ligase, at 12° C. for 16 h.

The pCRII vector is a cloning vector which contains single 3' deoxythymidylate overhangs that allows for direct ligation of PCR products, and both ampicillin and kanamycin resistance genes for selection in E. coli cells.

The construct (plasmid pCRII plus the insert) was then transfected and replicated in E. coli cells HB101.

Finally, the plasmid DNA was extracted from bacterial cells by the alkaline lysis method of Bimboim and Doly (Bimboim H. C., and Doly. J. (1979) *Nucleic Acids Research*, 7:1513) and purified by Nucleobond AX-100 cartridges (Macherey-Nagel GmbH, Duren, Germany).

Example 4

Construction of Plasmid pEMBL-SOD 374

The construct was prepared by using the pEMBLyex4 plasmid as a vector in which the previously isolated locus containing the SOD gene, the downstream, and the modified upstream regions were cloned.

Figure 2:
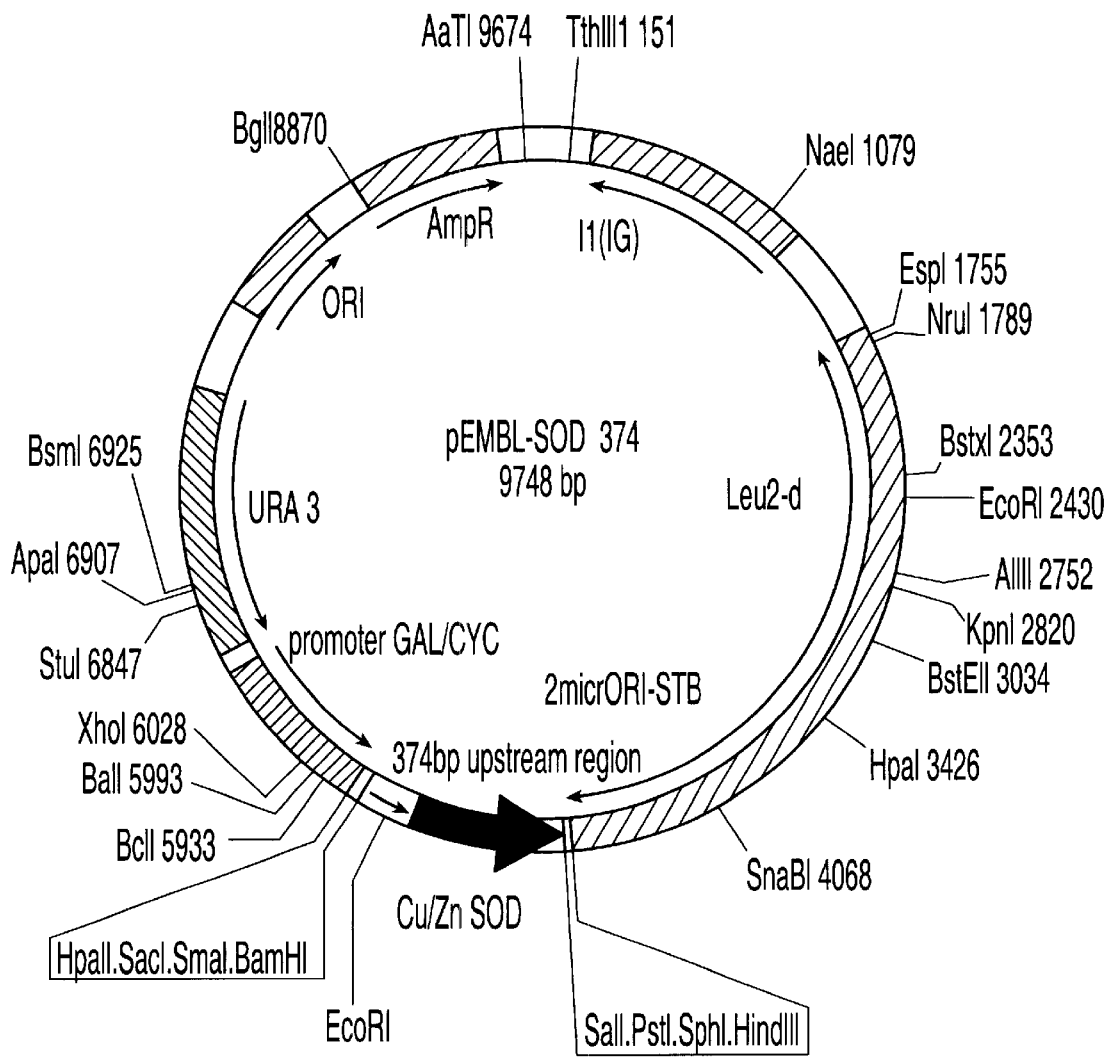
FIG. 2. Depiction of the plasmid construct pEMBL-SOD 374, derived from pEMBLyex4, with a 374 bp upstream region, the coding sequence and a downstream region of the yeast Cu/Zn SOD gene under the control of the yeast GAL/CYC promoter.

The construct was named pEMBL-SOD 374 and is shown in FIG. 2. It is a construct in which the subcloned fragment carries the coding region of the SOD gene (462 bp) and an upstream region of 374 bp.

To produce such a construct, the fragment which carries the Cu/Zn SOD gene, previously subcloned in pCRII plasmid, was directly excised by the restriction enzymes BamHI and SalI. This enzymatic digestion produced a BamHI-SalI 963 bp fragment which was purified by gel electrophoresis and subcloned into the BamHI-SalI sites of the vector pEMBLyex4.

Example 5

Preparation of Yeast Strains X4004 and GRF18 Transformed With pEMBL-SOD 374

Expression of the yeast Cu/Zn-SOD gene from the plasmid pEMBL-SOD 374 was tested following its insertion in two different strains of *S. cerevisiae* typically utilized for the expression of homologous or heterologous genes in yeasts (Martegani et al., *Appl. Microbiol. Biotechnology*, 37:604–608 (1992), Alberghina, L. et al., *Biotechnology and Applied Biochemistry*, 14:82–92 (1991), Pradyumna K. et al., Biotechnology and Bioeng. 40:235–246 (1992), Yong Soo Park et al., *Biotechnology and Bioeng.*, 41:854–861 (1993), Scott et al., *Biotechnology and Bioeng.*, 41:801–810 (1993), Jih-Han Hsieh et al., *Biotechnology and Bioeng.*, 32:334–340 (1988)).

The following haploid strains were used:

X4004, whose genotype is: MATa/lys5/ura3/met2/trp1; and

GRF18, whose genotype is: MATa/leu2–3,112/His3–11, 15.

These strains can be fermented at high biomass quite efficiently in selective or semisynthetic media due to the markers present on the plasmid pEMBLyex4 (LEU2-d and URA3) which complements, respectively, the leucine auxotrophy in the leu2-GRF 18 strain (the GRF18 strain carries a leu 2–3,112 double frameshift mutation that reverts extremely rarely) and the uracil auxotrophy of the ura3-X4004 strain.

Naturally, following insertion of the plasmid, the novel strains loses those specific auxotrophies. GRF 18, carrying the novel plasmid will still be auxotroph for histidine, while X4004, carrying the novel plasmid will still be auxotroph for methionine and tryptophane.

The yeast transformation with the plasmid constructs were performed as follows. Before transformation:

yeast strains (X4004 or GRF 18) were streaked on petri-plates in 10 mL of sterile distilled water a few cells were dissolved by scrapping them from the plate with a loop, Cells were sonicated for 5' and counted by Coulter Counter ($OD_{600}$ under 0.1), About $4 \times 10^7$ total cells were innuculated in 200 mL (giving $2–3 \times 10^5$ cells/mL, an $OD_{600}$ of about 0.6) of YEPD medium (in an 1 liter flask), Cells were grown for 16 h at 30° C. under mild shaking (about 6 generation) until about $-1 \times 10^7$ cells/mL ($OD_{600}=2-3$).

YEPD complete medium for routine growth of the cells before transformation was made as follows: 1% yeast extract, 2% peptone, 2% glucose, 2% Bacto agar (for petri-plates) and distilled water. All components were autoclaved for 20 min at 120° C.

Transformation was performed as follows: A total of $2 \times 10^8$ cells are used for a treatment (transformation of the strain with a 1 mg of plasmid DNA), for example, a total of $1 \times 10^9$ cells for 5 treatments (100 mL of culture broth containing $1 \times 10^7$ cells/ml). Transformation was carried out through the lithium chloride method of Ito modified by Schiestl and Gietz (R. H. Schiestl, R. D. Gietz, (1989), Current Genetics, 16:339–346). The transformants were plated on agar plates (synthetic minimal medium) lacking leucine (to select for plasmid-containing GRF 18 cells) or lacking uracil (to select for plasmid-containing X4004 cells) and grown at 30° C. Single colonies are stored either at 4° C. by streaking them on fresh selective plates or at –80° C. in 15% glycerol.

All the transformations were performed in duplicate on the basis of the following scheme:

| plasmid DNA (1 mL) | yeast strain ($2 \times 10^8$ cells) |
| --- | --- |
| pEMBL-SOD374 | X4004 |
| pEMBLyex4 | X4004 (negative control) |
| pEMBL-SOD 374 | GRF18 |
| pEMBLyex4 | GRF18 (negative control) |

Strain GRF 18 was grown on a synthetic medium without the amino acid leucine for the selection of plasmid-bearing strains, while in the case of X4004, the strain was grown on a synthetic medium without uracile.

The induction of expression in both cases was performed by shifting from minimal medium containing glucose to medium containing galactose as the carbon source as follows. The transformants, following streaking on plates, were grown in 50 mL of synthetic minimal medium (lacking leucine for transformed GRF18 or uracil for transformed X4004) containing 2% of glucose, at 30° C. for 12–14 h under mild shaking and aeration to reach about $2.5–3 \times 10^7$ cells/mL ($OD_{600}$ 4–5). 50 mL of selective synthetic medium, containing 2% of galactose, was inoculated with $5 \times 10^7$ cells (2 mL of preculture) to reach about $1 \times 10^6$ cells/mL. Growth was for about 17–18 h (about 7 generations) at 30° C. under mild shaking and aeration to reach about $2–3 \times 10^7$ cells/mL ($OD_{600}$ 4–5). $2 \times 10^8$ cells (e.g. about 10 mL of culture) were removed and used for protein extraction.

The medium to grow transformed cells was made as follows. Synthetic selective medium (to grow transformed X4004 cells): 2% of carbon source (glucose or galactose), 2% Bacto agar (for petri-plates), 50 mg/liter of L-lysineHCl, 50 mg/liter of L-methionine, and distilled water. Components were autoclaved for 20 min at 120° C., difco yeast nitrogen base (YNB)without amino acids was added (filtered concentrated stock solution 10X (67 g/liter)), 50 mg/mL of L-tryptophan (filtered concentrated stock solution).

Synthetic selective medium (to grow transformed GRFL8 cells): 2% of carbon source (glucose or galactose), 2% Bacto agar (for petri-plates), 50 mg/liter of L-histidine, distilled water. Components were autoclave for 20 min at 120° C., difco yeast nitrogen base (YNB) without amino acids was added (filtered concentrated stock solution 10X (67 g/liter)).

The ability of a microbial strain to produce a given polypeptide may be tested through several approaches.

Initially, it is advisable to evaluate the production of the simple polypeptide chain. In fact, the first question that has to be answered is whether the expression machinery of the novel cell is working efficiently in relation to the biosynthesis of the desired chemical entity. Thus, to test the presence of large amounts of a chemical entity like a polypeptide in cell extracts, total protein extracts are first run on SDS denaturing polyacrylamide gels which discriminate according to the molecular weight of the polypeptide chain.

To evaluate the expression of the polypeptide, the electrophoretic profile of a cell extract obtained from the plasmid-bearing strain may be compared with the cell extract obtained from a traditional strain that does not carry the SOD containing-expression plasmid (see negative controls).

Knowing the molecular weight of SOD (the SOD polypeptide chain is composed of 154 amino acids with a corresponding molecular weight of 15,700 Daltons), the two profiles were compared, in the region of the gel corresponding to the molecular weight of SOD, for the presence. Visualization was performed through non-specific staining with Coomassie-blue.

Evaluation of the productivity of the clones was using the analytical technique of SDS polyacrylamide electrophoresis as follows.

a) Protein Yeast Extraction.

The protocol that was used for preparation of total protein extracts from yeast, was partially modified from the method of Jazwinski (S. Michail Jazwinski, 1990, Methods in Enzymology, vol. 182 p. 154) as follows:

$2 \times 10^8$ cells were concentrated (in a 15 mL falcon tube) by centrifugation (4000 rpm at 4° C., 5 min), The pellet was washed with sterile water at 4° C. (transferred to eppendorf vials), The Pellet was resuspend in 400 microliters of 1X PBS buffer, 400 microliters of glass microbeads were added (prechilled at −20° C.), 4 microliters (1 mg/mL) of pepstatin was added (protease inibitor), vortexed for 3 min (twice on ice), 10 microliters of supernatant was stored at −20° C. for protein assay.

Staining of the gel with Coomassie blue gave a clear electrophoretic band in the samples (GRF18 cells transformed with plasmid pEMBL-SOD 374), corresponding to the molecular weight of the Cu/Zn SOD yeast protein loaded on the same gel.

Such bands were not observed in the negative control samples (GRF18 cells transformed with the plasmid pEMBLyex4 which does not carry the SOD gene and X4004 cells transformed with the plasmid pEMBLyex4 which does not carry the SOD gene). Approximately the same quantity of protein extracts for each sample (about 1 mg) was loaded on the polyacrylamide gel.

b) SOD Activity Determination by PIU-test.

The expression of a homologous or heterologous enzyme can be determined by an appropriate activity test. Therefore, the evaluation of the expression of yeast cells transformed by the two molecular constructs was performed by quantification of the SOD activity after induction of the cultures. The growth of the cultures were monitored by determining cell numbers with a counter (Coulter counter ZBI) Lotti et al., Appl Microbiol. Biotechnol. 28: 160–165 (1988)) or with measurement of absorbance at 600 nm. The protein extracts were prepared as described under "protein yeast extraction".

The presence of Cu/Zn SOD activity in total yeast cells extracts was detected by the method of Marklund and Marklund, based on the ability of the enzyme to inhibit the autoxidation of pyrogallol (Marklund S. and Marklund G., Eur. J Biochem. 47:469–474 (1974)).

The expression experiments were performed as batch fermentation in complete synthetic medium.

Complete synthetic medium (Sherman F., Methods in Enzymology. vol 194, Academic Press) with and without copper (0.0025 g/liter) and zinc (0.05 g/liter) was prepared as follows (in grams per liter): Bacto yeast Nitrogen base without amino acids (Difco Laboratories, Detroit, MI), 6.7; carbon source (glucose or galactose), 20; Adenine sulfate, 50; uracil, 50; L-tryptophan, 50; L-histidine, 50; L-arginine-HCl, 50; L-methionine, 50; L-tyrosine, 50; L-isoleucine, 50; L-lysine-HCl, 50; L-phenylalanine, 50; L-glutamic acid, 50; L-aspartic acid, 50; L-valine, 50; L-threonine, 50; L-serine, 50.

Table 1 shows SOD activity data (in strain GRF18) of three experiments and the mean values upon expression of the SOD gene before deletion of MCS and bacterial sequences:

TABLE 1

| Transformants | 1. PIU/mL | 2. PIU/mL | 3. PIU/mL | Mean values |
|---|---|---|---|---|
| pEMBL SOD 374 (in GRF 18) | 575 | 168 | 180 | 301 |
| pEMBLyex4 (in GRF 18) | 18 | 10 | 12 | 13 |
| Purchased Wine Yeast | 22 | — | | 22 |

The average expression values are 301 PIU/mL for the vector pEMBL-SOD 374, and 13 PIU/mL for the vector pEMBLyex4 (without the insert). These values are important to judge the specific expression of the target gene. They were determined in standardized laboratory batch fermentations. The results show on average a 23 times elevated expression level compared to the original strain (GRF 18 with plasmid but without insert). Compared to a purchased wine yeast strain ("Seccoferm") a 22-fold increase in expression was observed in the laboratory batch assays. It was shown that the economy of the manufacturing process was highly increased by the new constructions.

Example 6

Preparation of the Vector pEMBL-SOD 374 w/o MCS

The conclusion can be taken from Example 5 that the performance of the yeast strain GRF 18, containing the molecular construct pEMBL-SOD 374, was very high, as control was the same strain which did not contain any construct. Thus, the molecular construct pEMBL-SOD 374 was used to build the final expression system by deleting any non-yeast sequence.

The synthetic sequence of the "multiple cloning site" was completely deleted by a digesting both ends of the polylinker with the enzymes SstI and HindIII. This operation permitted the excision of the entire 95 bases of the artificial sequence from the molecular construct pEMBL-SOD 374 and allowed fpr insertion of the complete yeast Cu/Zn SOD gene between the remaining natural sites.

Detailed Protocol:

1) The clone pEMBL-SOD 374 was cut by the enzymes HindIII (New England Biolabs Inc., USA) and SacI (New England Biolabs Inc., USA) to excise the polylinker from the rest of the vector. The enzyme HindIII recognizes the unique site "A/AGCTT" at one end of the multiple cloning site, while the enzyme SacI is a isoschizomer of the enzyme SstI and recognizes the same unique sequence "GAGCT/C" at the other end of the multiple cloning site.

Following this double digestion, a HindIII-SacI fragment of 8705 bases which carries all the yeast and bacterial sequences of the vector pEMBL without the polylinker, was isolated from agarose gel by electroelution.

The 8705 bp-fragment was finally purified by phenol-chloroform treatment and concentrated by ethanol precipitation.

2) The ends of the 8705 bp HindIII-SacI fragment were treated with the enzyme Polymerase 1 "Klenow fragment" to create compatible ends on the fragment for further manipulations. This treatment creates blunts ends on the fragment by filling of the HindIII end (which is the 5' protuding termini) and cutting of the SacI end (which is the 3' protuding termini).

Finally, the blunt-ended fragment was purified by phenol-chloroform and ethanol precipitation.

3) The DNA fragment carrying the yeast Cu/Zn SOD gene present on pEMBL-SOD 374 was cut with the enzymes EcoRI (New England Biolabs Inc., USA) and SalI (New England Biolabs Inc., USA) which recognize respectively the sites "G/AATTC" and "G/TCGAC". This double digestion permits the isolation of a fragment of 916 bp which carries a 342 bp yeast upstream sequence, the entire open reading frame of the yeast Cu/Zn SOD gene of 462 bp and a yeast downstream sequence of 112 bp. This 916 bp fragment, which does not carry any other bacterial or artificial sequence, was isolated from agarose gel by electroelution. The fragment was further purified by phenol-chloroform treatment and ethanol precipitation.

4) After purification, the EcoRI-SalI fragment was treated with the enzyme Polymerase I "Klenow fragment" which performs the filling of the EcoRI and SalI ends (which are both 5' protuding termini) to make them compatible to the subcloned ends of the purified pEMBL vector from which the polylinker was previously deleted. The blunt-ended fragment was again purified by phenol-chloroform and ethanol precipitation.

5) The blunt-ended 916 bp fragment containing the yeast Cu/Zn SOD gene was finally subcloned into the blunt-ended 8705 bp fragment-pEMBL vector by ligation with the enzyme T4 DNA Ligase (Boehringer Mannheim GmbH, Mannheim). The ligation was performed at 16° C. for 20 h.

6) After transformation of the ligation mixture (blunt-ended 916 bp fragment plus blunt-ended 8705 bp fragment) in *E. coli* (XL 1-Blue strain), a random screen was performed to isolate the clones which carry the right sequences. A number of bacterial clones from the transformation were grown overnight at 37° C. in LB broth medium and the DNA plasmids from the clones was extracted by the "mini prep" method ("Wizard" minipreps DNA purification system, Promega Corp., USA).

PCR amplification as well as DNA sequencing were used to verify both the presence and the correct orientation of the fragment containing the yeast Cu/Zn SOD gene in the clones.

The correctness was confirmed by sequencing and agarose gel electrophoresis.

Example 7

Preparation of the Final Vector pEMBL-SOD w/o MCS w/o Coli

The clone "pEMBL-SOD 374 w/o MCS" obtained from Example 6 carries only the yeast sequences (yeast funtional sequences and yeast Cu/Zn SOD gene) and the bacterial sequences. The non-yeast part of the "pEMBL-SOD 374 w/o MCS" clone carries the origin of replication for the bacterium *Escherichia coli*, the ampicilline bacterial selectable marker and the origin of replication derived from the filamentous bacteriophage f1.

This region covers more than 4000 bases and must be deleted by enzymatic digestion in order to obtain a final vector which carries only yeast sequences. The final vector following such a manipulation will be able to replicate only in yeast strains. In fact, the only sequences present in the final vector are:

the Leu 2-d yeast selectable marker useful to select the yeast cell transformants, the origin of replication of 2-micron yeast episome that provides high mitotic stability and replication of the plasmid, the entire yeast expression hybrid UAS GAL/CYC system that provides high level of transcription of the gene under its control, the yeast SOD gene (with upstream and downstream functional yeast sequences) which produces the enzyme Cu/Zn Superoxide Dismutase.

The following is a detailed protocol for preparation of vector.

1) The clone "pEMBL-SOD 374 w/o MCS", previously deleted from the multiple cloning site, was digested with the blunt endonucleases StuI (in position 5942 of the original pEMBLyex4 vector) and NruI (in position 1791 of the original pEMBLyex4 vector). The enzyme StuI (Pharmacia, Uppsala) recognizes the unique blunt site "AGG/CCT" and the enzyme NruI (Pharmacia, Uppsala) recognizes the unique blunt site "TCG/CGA". The resulting StuI-NruI fragment of 4689 bp carrying all the bacterial sequences was separated from the rest of the pEMBL vector by gel electrophoresis. The double digestion also deletes part of the yeast selectable marker URA 3 on the vector but it preserves the complete function of the other yeast selectable marker LEU-2d, which may be used for the selection of clones during further manipulations.

2) The fragment pEMBL vector containing only yeast sequences and the yeast Cu/Zn SOD gene were isolated from agarose gel by electroelution and purified by phenol-chloroform and ethanol precipitation.

3) The ends of the purified pEMBL vector (both ends are blunt) were rejoined together by the enzyme T4 DNA ligase (Boehringer Mannheim GmbH, Mannheim) and the ligation mixture was used to transform the yeast strain GRF 18.

4) Clones from the transformation were plated on agar plates with synthetic minimal medium lacking leucine for selection (by the selectable marker Leu 2-d) of the GRF 18 cells containing the plasmid.

5) A number of yeast colonies obtained from the transformation were tested by PCR to confirm both the presence of the yeast fragment containing the yeast Cu/Zn SOD gene and the absence of any bacterial sequence between the StuI and NruI enzymatic sites. To confirm the presence of the yeast fragment on the final construct "pEMBL-SOD w/o MCS w/o Coli", PCR amplification was performed with the two flanking primers SOD proA and SOD proB. An electrophoretic band of about 1133 bp length confirmed the presence of the fragment containing the yeast Cu/Zn SOD gene in six yeast clones.

The correctness was confirmed by sequencing and agarose gel electrophoresis.

Figure 3:
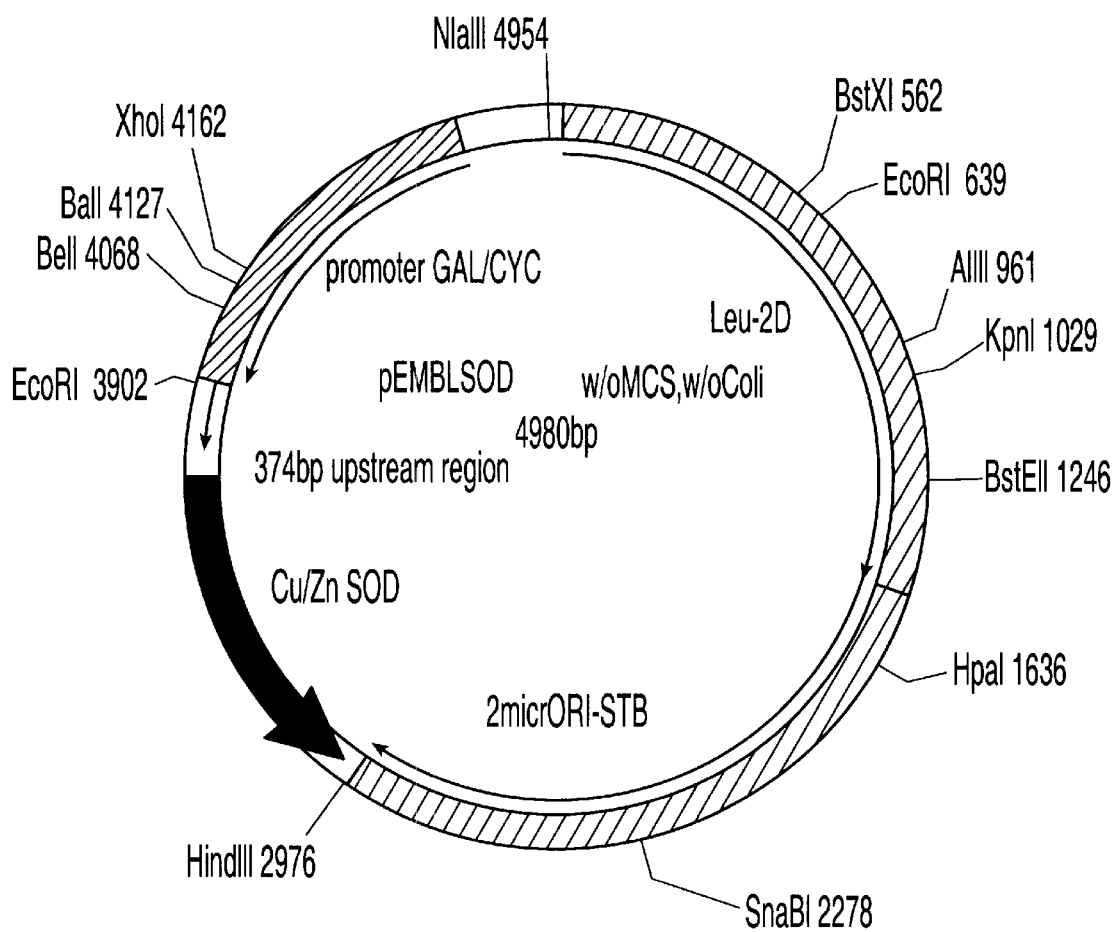
FIG. 3. Depiction of a map of the final plasmid pEMEL-SOD without sequences from multiple cloning sites or Esherichia coli comprising a 374 upstream region, the coding sequence and a downstream region of the yeast Cu/Zn SOD gene between the restriction sites EcoRI and HindIII, under the control of the yeast GAL/CYC promoter, it is comprised of only yeast sequences and replicates only in yeast.

The final vector "pEMBL-SOD w/o MCS w/o Coli" derived from such manipulations does not carry any bacterial or artificial sequence and will be able to replicate only in yeast strains because of the presence of only yeast sequences. The final vector is presented as a restriction map in FIG. 3.

Example 8

Evaluation of the Expression of the Yeast Cu/Zn SOD Gene in the New Yeast Strain This example relates to the evaluation of the expression of the yeast Cu/Zn SOD gene in the new yeast strains as constructed in Examples 6 and 7. All the experiments were performed as in Example 5 by growing yeast cells in complete synthetic media.

Table 2 shows the presence of SOD activity in total yeast cell extracts upon expression of SOD gene after deletion of MCS and bacterial sequences in GRF 18-pEMBL SOD 374 in complete synthetic medium.

TABLE 2

| Transformants | PIU/mL |
| --- | --- |
| pEMBL-SOD 374 (in GRF 18) | 138 |
| pEMBLyex4 (in GRF 18) | 17 |
| pEMBL-SODw/oMCSw/oColi (in GRF 18) | 141 |

The test results indicated that the vector pEMBL-SODw/oMCSw/oColi expresses the yeast Cu/Zn SOD gene in higher yield compared to vector pEMBLyex4 (in GRF 18).

Example 9

Isolation and purification of yeast Cu/Zn SOD

The production of the target polypeptide, such as the yeast superoxide dismutase, is performed under aerobic conditions in computer-controlled fermenters, for example, according to Alberghina et al. ibid. Controlled parameters of fermentation are temperature, dissolted oxygen, pH and ethanol concentration.

The purification of the polypeptide is comprisesd the following steps:

1. The yeast cells in the fermentation broth is directly lysed by homogenization with a homogenizer (e. g. an APV Gaulin) at a temperature of between 20 and 30° C., a pressure of between 600 and 800 bar and 3 cyles, or with a dynobed mill (e. g. a Dyno Mill Model KDL) filled with acid washed 0.3 mm diameter, and recirculating the suspension through the mill at 160 ml/mm for 1–2 mm at room temperature.

2. The separation of cell debris and proteins is performed by centrifugation (e. g. with a Beckmann J2–21 centrifuge with JA-10 fixed angle rotor for 60 mm at a speed of 14,000 g), or by microfiltration, (e. g. by tangential flow filtration with Minitan (Millipore Corp., Bedford)) equipped with a 0.45 pm cut-off membrane.

3. Protein was concentrated and buffer exchanged by ultrafiltration and diafiltration (for example Tangential flow filtration with Minitan (Millipore Corp., Bedford)) equipped with a 10,000 Dalton cut-off cellulose membrane (PLGCOMP 04 membrane). Exchange Buffer was 20 mM Tris-HCl pH 8.0.

4. Purification by cationic exchange chromatography (e. g. with DEAE-Sepharose). Loading buffer: 20 mM Tris-HCl pH 8.0. Elution buffer: 20 mM Tris-HCl pH 8.0, 1 M NaCl.

5. Concentration and buffer change by ultrafiltration and diafiltration to obtain the final buffered SOD solution. Conditions: a Tangential flow filtration with Minitan (Millipore Corp., Bedford) equipped with a 10,000 Dalton cut-off membrane. Buffer: 20 mM Tris-HCl, pH 8.0.

At the end of fermentation the activity is at least 5000 PIU/mL. The yield obtainable with the new strain according to the invention is at least 10 times higher compared to the yield obtainable with purchasable bakers yeast. From 1 g bakers yeast 5000 PIU can be isolated, whereas at least 40,000 PIU can be isolated from 1 g pEMBL-SOD 374 GRF 18 yeast.

What is claimed is:

1. An isolated expression vector construct for the production of a yeast or a non-yeast polypeptide in yeast comprising:
   (A) a DNA sequence encoding said polypeptide; and
   (B) DNA sequences allowing for expression of the polypeptide in yeast, wherein said vector, except for any DNA sequences coding for non-yeast polypeptides, lacks any non-yeast DNA sequences.

2. The vector construct according to claim 1 wherein the DNA sequence encoding said polypeptide is a yeast DNA sequence and is under the control of a yeast promoter.

3. The vector construct according to claim 1 consisting essentially of:
   (A) a DNA sequence encoding a polypeptide;
   (B) a promoter in reading frame with the coding sequence; and
   (C) one or more DNA sequences selected from the group consisting of an ori, a leader sequence, a terminator, and a DNA sequence encoding a polypeptide for selection of the vector construct.

4. The vector construct according to claim 1 comprising a yeast Cu/Zn SOD polynucleotide coding sequence under the control of a GAL/CYC promoter.

5. The vector construct according to claim 1 consisting essentially of the following sequences:
   (A) a Leu 2-d yeast selectable marker;
   (B) the origin of replication of the 2-micron yeast episome;
   (C) the entire yeast expression hybrid promoter cassette UAS GAL/CYC; and
   (D) the yeast SOD gene with upstream and downstream functional yeast sequences, which vector construct produces the enzyme Cu/Zn superoxide dismutase.

6. The vector construct according to claim 1, wherein the DNA sequence encoding said polypeptide is a non-yeast DNA sequence under the control of a yeast promoter.

7. The vector construct according to claim 1, wherein the DNA sequence encoding said polypeptide is a human or animal DNA sequence under the control of a yeast promoter.

8. A yeast strain transformed with the vector construct according to claim 1.

9. A yeast strain transformed with the vector construct according to claim 5.

10. A method for the production of a yeast strain comprising transforming a yeast strain with a vector construct according to claim 1.

11. A method for the production of a polypeptide in a yeast strain comprising growing a yeast strain transformed with a vector construct according to claim 1 in a medium and isolating the polypeptide.

12. A method for the production of the enzyme Cu/Zn Superoxide Dismutase in a yeast strain, comprising preparing a yeast strain according to the method of claim 10, growing the strain in a medium, and isolating the enzyme.

13. A method for the production of an expression vector, comprising the step of:
   extracellular excision of all non-yeast sequences from a shuttle vector capable of expressing a first polypeptide in a yeast strain to obtain a vector that, except for any DNA sequences coding for non-yeast polypeptides, lacks any non-yeast DNA sequences.

14. The method of claim 13 further comprising the step of replacing the DNA sequence coding for the first polypeptide by a sequence coding for a second polypeptide.

15. An isolated expression vector construct for the production of a yeast polypeptide comprising:
   a) a yeast Cu/Zn SOD polynucleotide coding sequence under the control of a GAL/CYC promoter; and
   b) a plurality of DNA sequences allowing for expression of the polypeptide in yeast, wherein the vector construct lacks any non-yeast DNA sequences.

16. The isolated expression vector construct of claim 15, wherein the coding sequence is a non-yeast DNA sequence under the control of a yeast promoter.

17. A yeast strain transformed with the vector construct of claim 15.

18. A method for the production of an expression vector comprising the steps of:
   providing a shuttle vector that expresses a first polypeptide in a yeast strain;
   extracellularly excising all non-yeast sequences from the shuttle vector, wherein DNA sequences coding for non-yeast polypeptides, if present, are not excised; and subsequently cloning the shuttle vector lacking any non-yeast sequences, thereby producing the expression vector.

19. The vector construct according to claim 4, wherein the Cu/Zn SOD polynucleotide coding sequence is from Saccharomyces cerevisiae.

20. An isolated expression vector construct for the production of a yeast polypeptide in yeast comprising:

(A) a DNA sequence encoding said yeast polypeptide; and (B) DNA sequences allowing for expression of the yeast polypeptide in yeast, wherein said vector construct lacks any non-yeast DNA sequences.

21. An isolated expression vector construct for the production of a non-yeast polypeptide in yeast comprising:

(A) a DNA sequence encoding said non-yeast polypeptide; and (B) DNA sequences allowing for expression of the non-yeast polypeptide in yeast, wherein said vector construct, except for any DNA sequences coding for said non-yeast polypeptide, lacks any non-yeast DNA sequences.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence -continued

```
<220> FEATURE:
<223> OTHER INFORMATION: Oligonucleotide Primer

<400> SEQUENCE: 1
ggacgtaagc atctctgaag tg                                              22

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 2
gccgtcgacg gacccctcaa gacccctc                                        28

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 3
gccgtcgaca cacttggtga atgatcaagg                                      30
```